United States Patent [19]

Bernardi et al.

[11] 4,077,969
[45] Mar. 7, 1978

[54] PROCESS FOR PREPARING AZETIDINONE THIAZOLIDINE DERIVATIVES

[75] Inventors: Luigi Bernardi; Maurizio Foglio; Giovanni Francheschi, all of Milan, Italy

[73] Assignee: Societa' Farmaceutici Italia S.p.A., Milan, Italy

[21] Appl. No.: 587,090

[22] Filed: Jun. 16, 1975

[30] Foreign Application Priority Data

Jun. 21, 1974  Italy .................. 24249/74

[51] Int. Cl.² .......................... C07D 513/04
[52] U.S. Cl. ............................. 260/306.7 C
[58] Field of Search ................. 260/306.7 C

[56] References Cited

U.S. PATENT DOCUMENTS 3,483,216  12/1969  Woodward ............... 260/306.7 C
3,900,487  8/1975  Underwood et al. ....... 260/306.7 C

OTHER PUBLICATIONS

Brown, "Organic Synthesis Via Boranes," 1975, pp. 1-3, and 23.

*Primary Examiner*—Donald G. Daus
*Assistant Examiner*—David E. Wheeler
*Attorney, Agent, or Firm*—Stevens, Davis, Miller & Mosher

[57] ABSTRACT

A process is disclosed for preparing azetidonethiazolidines of the formula

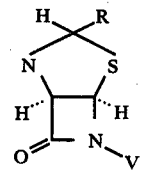

where R and V are defined herein below, wherein a compound of the structure

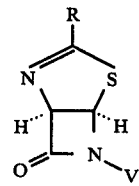

dissolved in a suitable solvent, is treated at about 0° C with a solution of preferably anhydrous hydrochloric acid in a lower aliphatic alcohol with a slight excess of sodium cyanoborohydride.

2 Claims, No Drawings

PROCESS FOR PREPARING AZETIDINONE THIAZOLIDINE DERIVATIVES

DESCRIPTION OF THE INVENTION

A process is disclosed for preparing azetidone-thiazolidine derivatives of structure:

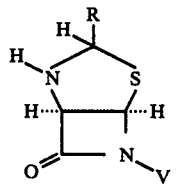
(II)

where V may be hydrogen, or a saturated or unsaturated aliphatic residue with or without substituents, or an aromatic, arylaliphatic or acyl residue, and in particular the residues:

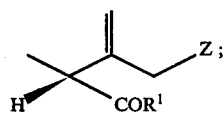

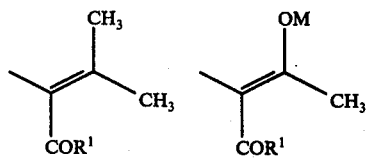

where R is selected from the class consisting of hydrogen, alkyl with not more than 12 carbon atoms, cycloalkyl with not more than 12 carbon atoms, alkenyl with not more than 12 carbon atoms, with or without various substituents of the free or protected hydroxyl type, free or blocked amino, cyano or nitro groups, or from the radicals thienyl-methyl, furyl-methyl, naphthyl-methyl, cyclohexyl-methyl, cyclohexadienyl-methyl, or from the following groups:

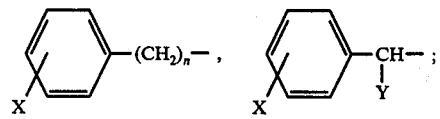

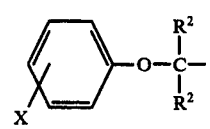

in which
X is hydrogen, halogen, free or protected hydroxyl, alkyl with 1 to 4 carbon atoms, or a protected amino, nitro or cyano group;
Y is a protected hydroxyl, amino or carbonyl group;
n is an integer from 0 to 4;
M is hydrogen, or an alkyl group with 1 to 4 carbon atoms; an arylalkyl group with 7 to 9 carbon atoms, or a mesyl, tosyl, acyl or acyloxy group;
$R^1$ is selected from the class consisting of hydroxyl, alkoxy with 1 to 4 carbon atoms, benzyloxy, p-methoxy-benzyloxy, p-nitrobenzyloxy, benzidryloxy, triphenylmethoxy, phenacyloxy, p-halo-phenacyloxy, phthalimidomethoxy, free amino or amino substituted by an alkyl group with 1 to 4 carbon atoms, cycloalkyl groups with 5 to 8 carbon atoms, phenyl, heterocyclic mononuclear, acyloxymethyloxy, acylamidomethyloxy, and a free or substituted hydrazino group;
Z is selected from the class consisting of hydrogen, hydroxy, $-O-$alkyl $-O-CO-$alkyl, $-Br$, $-I$, $-N_3$, $-NH_2$, $-O-CO-CH_3$, $O-CO-NH_2$, -S-alkyl where the alkyl group has 1 to 4 carbon atoms, and a nitrogenous -S-heterocyclic mononuclear ring; and
$R^2$ is independently or together selected from the class consisting of hydrogen and an alkyl group with 1 to 4 carbon atoms, wherein a compound of structure:

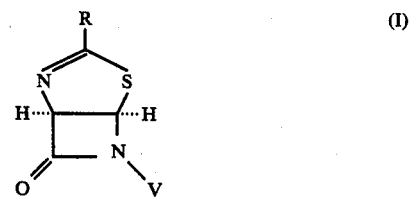
(I)

where R and V have the meanings given heretofore, dissolved in a suitable solvent such as dioxane, tetrahydrofuran, or lower aliphatic alcohols such as methanol or ethanol, alone or in admixture, is treated at a temperature of about 0° C with a solution of preferably anhydrous hydrochloric acid in a lower aliphatic alcohol and with a slight excess of sodium cyanoborohydride, keeping the reaction mass under stirring for 20–30 minutes, and after the excess of reagent is eliminated by adding dilute acids, the compound (II) thus formed is isolated and purified.

This invention relates to a process for preparing β-lactam derivatives.

More particularly, this invention relates to an entirely novel process for preparing azetidone-thiazolidine derivatives of structure (II) starting from the corresponding azetidonethiazoline derivatives of structure (I) in accordance with the following equation:

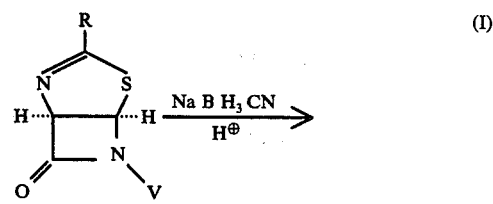

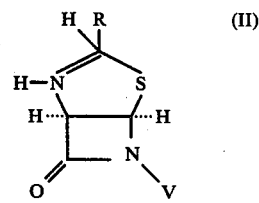

where, apart from the other substituents, V may be hydrogen, or a saturated or unsaturated aliphatic residue with or without substituents, or an aromatic arylaliphatic or acyl residue, and in particular the residues

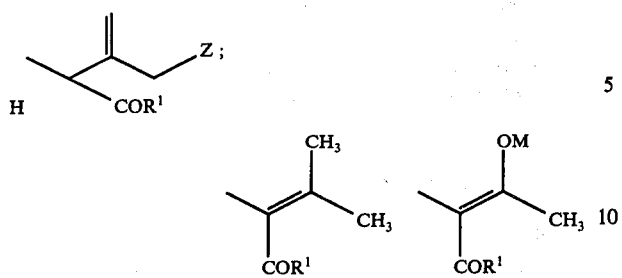

where R is selected from the class consisting of hydrogen, alkyl, cycloalkyl, alkenyl with not more tha 12 carbon atoms, with or without various substituents of the free or protected hydroxyl type, free or blocked amino, cyano or nitro groups, or from the radicals thienyl-methyl, furyl-methyl, naphthyl-methyl, cyclohexyl-methyl, cyclohexadienyl-methyl, or from the following groups:

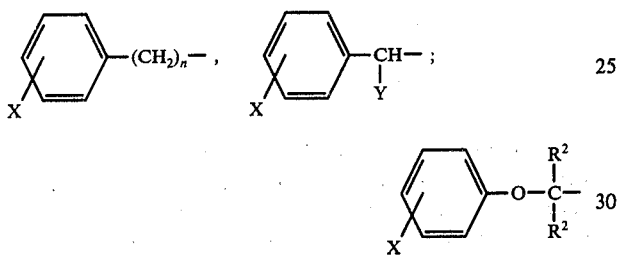

in which
X is hydrogen, halogen, free or protected hydroxyl, alkyl with 1 to 4 carbon atoms, or a protected amino, nitro or cyano group;
Y is a protected hydroxyl, amino or carboxyl group;
$n$ is an integer from 0 to 4;
M is hydrogen or an alkyl group with 1 to 4 carbon atoms, an arylalkyl group with 7 to 9 carbon atoms, or a mesyl, tosyl, acyl or acyloxy group;
$R^1$ is selected from the class consisting of hydroxyl, alkoxy with 1 to 4 carbon atoms, benzyloxy, p-methoxy-benzyloxy, p-nitrobenzyloxy, benzidryloxy, triphenylmethoxy, phenacyloxy, p-halophenacyloxy, phthalimidomethoxy, free amino or amino substituted by an alkyl group with 1 to 4 carbon atoms, cycloalkyl groups with 5 to 8 carbon atoms, phenyl, heterocyclic mononuclear, acyloxymethyoxy, acylamidomethyloxy, and a free or substituted hydrazino group;
Z is selected from the class consisting of hydrogen, hydroxyl, —O—alkyl, —O—CO-alkyl, —Br, —I, —N₃, —NH₂, —O—CO—CH₃, O—CO—NH₂, -S-alkyl where the alkyl group has 1 to 4 carbon atoms, and a nitrogenous -S-heterocyclic mononuclear ring; and
each $R^2$ is independently or together selected from the class consisting of hydrogen and an alkyl group with 1 to 4 carbon atoms.

It is known from the literature (R.D.G. Cooper et al., J.A.C.S. 94, 1972, p.1021) that an azetidinone-thiazolidine of structure (II) where V is hydrogen and R is —CH₂—O—C₆H₅ may be obtained by reducing the corresponding azetidinone-thiazoline with an aluminum amalgam in wet ether. This method, however, is not selective in reducing the double thiazolinic bond and may easily lead to hydrogenolysis. Furthermore, reduction with aluminum amalgam leads to considerable difficulties in separating the desired products from the gelatinous aluminum hydroxide mass.

It has not been surprisingly found — and this constitutes the object of the present invention — that the reduction of compounds of structure (I) to compounds of structure (II) may advantageously be carried out with sodium cyanoborohydride, operating in an acid environment and under non-hydrogenolytic conditions.

The reaction is very rapid and highly selective, and therefore it is of wide application to compounds of structure (I) without undesirable side reactions.

The sodium cyanoborohydride is used in slight excess, generally from 2 to 4 equivalents. This excess does not give rise to undesirable side reactions and is rapidly destroyed by adding dilute acids at the end of the reaction.

The initial azetidinone-thiazoline (I) is dissolved in a suitable solvent such as dioxan, tetrahydrofuran, or lower aliphatic alcohols such as methanol or ethanol, alone or in admixture, and is cooled to around 0° C. A solution of preferably anhydrous hydrochloric acid in a lower aliphatic alcohol and a slight excess of sodium cyanoborohydride are then added to this cooled solution under stirring.

The reaction occurs rapidly in a few minutes, but generally it is preferred to complete it by leaving the mass under stirring in the cold for 20-30 minutes. The solvent is evaporated under vacuum to dryness. The residue is redissolved under shaking in dilute aqueous acid and a suitable solvent immiscible with water, such as methylene chloride, and the organic layer is separated. The organic layer is evaporated to dryness under vacuum. The residue is then recrystallised from a suitable solvent.

The following examples serve to illustrate the invention without, however, limiting it.

EXAMPLE 1

Methyl-α-isopropenyl-3-phenoxymethyl-1α,5α-4-thia-2,6-diaza[3,2,0]-heptane-6-acetate-7-one (IV)

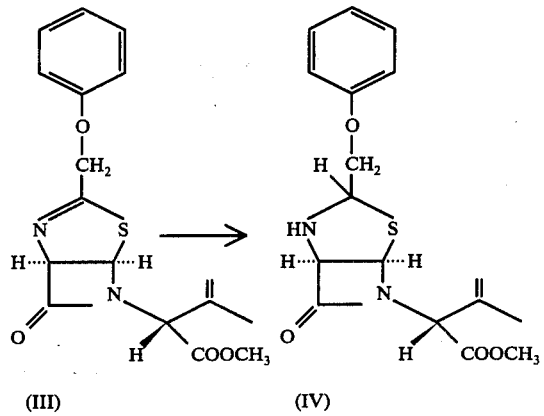

A solution of 0.346 g of methyl-α-isopropenyl-3-phenoxymethyl-1α,5α-4-thia-2,6-diaza[3,2,0]-2-heptene-6-acetate-7-one (III) in 15 ml of methanol and 5 ml of tetrahydrofuran, is cooled to 0° C. 0.6 ml of a 5N solution of hydrochloric acid in anhydrous methanol and 150 mg of sodium cyanoborohydride are then added. After 20 minutes, the solvent is evaporated and the residue dissolved in methylene chloride and water.

The organic layer is washed well with water, and then dried over sodium sulphate to give a residue which is crystallised from ethyl ether. In this manner, 0.320 g of product (IV) are obtained, m.p. 103°–104° C.

NMR (CDCl₃): 1.92 (s, 3H,

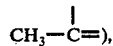

2.67 (broad s, 1H, NH), 3.81 (s, 3H, CH₃OCO), 4,4–4,6 (m, 2H, CH₂—C(H)), 4.7–4.9 (m, 1H, CH—C(H₂)), 4.80 (s, 1H, N—CH—COO), 5.0–5.2 (m, 2H, =CH₂), 5.26 (broad d, J = 4.0Hz; 1H, C(1)H), 5.89 (d, J = 4.0Hz, 1H, C(5)H) and 6.85–7.50 δ(m, 5H, C₆H₅).

IR (KBr): 1755 cm⁻¹ (C=O β-lactam); 1740 cm⁻¹ (C=O ester).

EXAMPLE 2

Methyl-α-1'-hydroxyethylidene-3-phenoxymethyl-1α,-5α-4-thia-2,6-diaza[3,2,0]-heptane-6-acetate-7-one (VI)

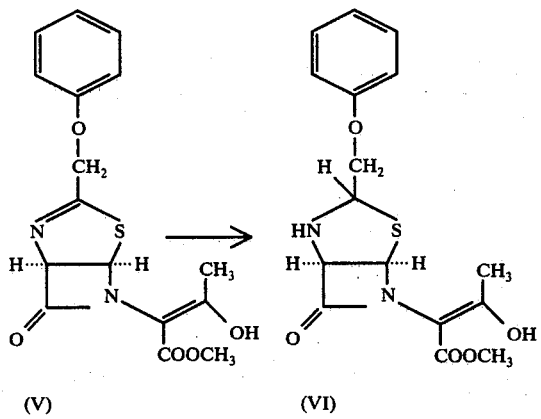

A solution of 0.350 g of methyl-α-1'-hydroxyethylidene-3-phenoxymethyl-1α,5α-4-thia-2,6-diaza[3,2,0]-2-heptene-6-acetate-7-one (V) in 15 ml of methanol and 5 ml of tetrahydrofuran is cooled to 0° C and to this are added 3 ml of a 1.8N solution of hydrochloric acid in methanol and 0.120 g of sodium cyanoborohydride. The solvent is evaporated and water and methylene chloride are added. The organic layer is washed well with water, and dried and evaporated.

The residue is crystallized from methanol - methylene chloride, to give 0.280 g of the product (VI) with an m.p. of 192°–195° C.

NMR (CDCl₃): 2.08 (s, 3H,

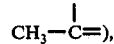

2.54 (broad s, 1H, NH), 3.78 (s, 3H, CH₃OCO), 4.25–4.55 (m, 2H, CH₂—C(H)), 4.65–4.95 (m, 1H, CH—C(H₂)), 5.26 (broad d, J = 4.0Hz, 1H, C(1)H), 5.75 (d, J = 4.0Hz, 1H, C(5)H), 6.80–7.50 (m, 5H, C₆H₅) and 12.22 δ(s, 1H, OH).

IR (CHCl₃): 1765 cm⁻¹ (C=Oβ-lactam); 1660 cm⁻¹ (C=O ester).

EXAMPLE 3

Methyl-α-1'-hydroxyethylidene-3-phenoxymethyl-1α,-5α-4-thia-2,6-diaza[3,2,0]-heptane-6-acetate-7-one (VI)

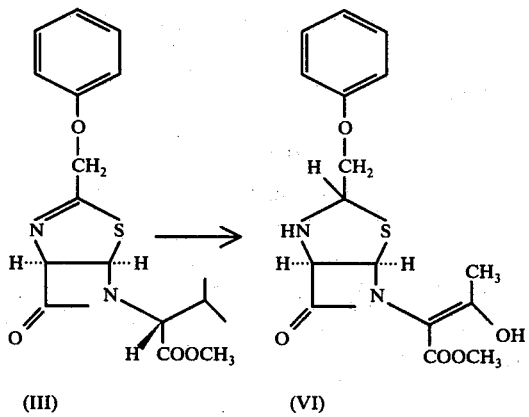

A solution of 1.9 g of methyl-α-isopropenyl-3-phenoxymethyl-1α,5α-4-thia-2,6-diaza[3,2,0]-2-heptene-6-acetate-7-one (III) in 100 ml of methylene chloride is cooled to −70° C and ozonised with a current of O₃/O₂ until violet coloration is obtained. Nitrogen is passed into the mixture for 10 minutes and the solvent is evaporated at room temperature. The residue is dissolved in 50 ml of methanol and 20 ml of tetrahydrofuran, cooled to 0° C, and 7 ml of a solution of 1.36N hydrochloric acid in methanol and 1.0 g of sodium cyanoborohydride are added. After 10 minutes under stirring the solvent is evaporated and the residue taken up with methylene chloride and water.

The organic layer dried over sodium sulphate, is evaporated and crystallised from methanol-methylene chloride, to give 1.5 g of product (VI), m.p. 192°–195° C.

EXAMPLE 4

Methyl-α-1'-methoxyethylidene-3-phenoxymethyl-1α,-5α-4-thia-2,6-diaza[3,2,0]-heptane-6-acetate-7-one (VIII)

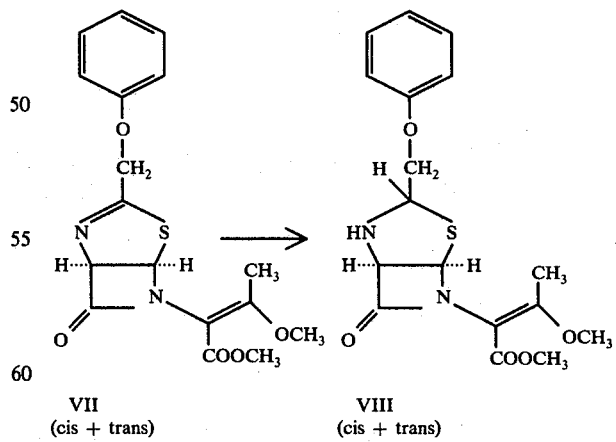

A solution of 0.700 g of methyl-α-1'-methoxyethylidene-3-phenoxymethyl-1α,5α-4-thia-2,6-diaza[3,2,0]-2-heptene-6-acetate-7-one (VII), comprising a 1:1 mixture of cis:trans isomers, in 15 ml of methanol and 10 ml of tetrahydrofuran, is cooled to 0° C, and to this are added 2.5 ml of a 1.3N solution of hydrochloric acid in methanol and 0.400 g of sodium cyanoborohydride. After 15 minutes under stirring, the solvent is evaporated under vacuum and methylene chloride and water added.

The organic layer, dried over sodium sulphate, gives a residue of 0.620 g of product (VIII) in the form of a cis-trans mixture, Rf 0.16 [m/e 364 (M+)] and Rf 0.21 [m/e 364 (M+)] in the benzol:benzin:ethyl acetate = 25:5:70 system, on a thin layer of silica gel.

EXAMPLE 5

Methyl-α-isopropylidene-3-phenoxymethyl-1α,5α-4-thia-2,6-diaza[3,2,0]-heptene-6-acetate-7-one (X)

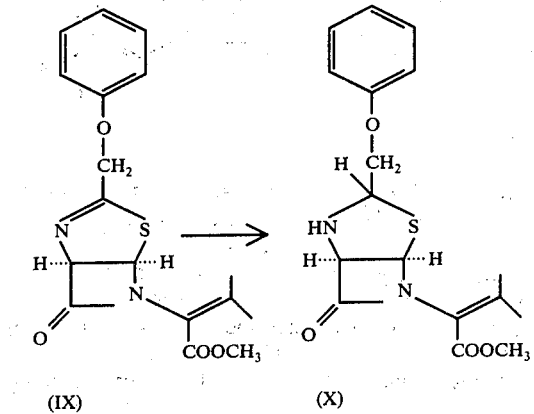

A solution of 0.400 g of methyl-α-isopropylidene-3-phenoxymethyl-1α,5α-4-thia-2,6-diaza[3,2,0]-2-heptene-6-acetate-7-one (IX) in 20 ml of methanol and 8 ml of tetrahydrofuran, is cooled to 0° C. To this are added 4 ml of a 2N solution of hydrochloric acid in methanol and 0.200 g of sodium cyanoborohydride.

After stirring for 10 minutes, the solvent is evaporated, methylene chloride and water are added and the organic layer is separated which, after drying over sodium sulphate, gives a crystalline residue of 0.320 g of product (X), m.p. 209°–210° C.

NMR (CDCl₃):

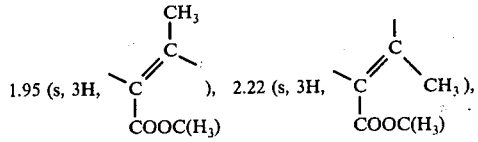

2.69 (broad s, 1H, NH), 3.75 (s, 3H, CH₃OCO), 4.40–4.60 (m, 2H, CH₂—C(H)), 4.80–5.00 (m, 1H, CH—C(H₂)), 5.25 (broad d, J = 4.0Hz, 1H, C(1)H), 5.83 (d, J = 4.0Hz, 1H, C(5)H) and 6.80–7.50δ(m, 5H, C₆H₅).

IR (CHCl₃): 1755 cm⁻¹ (C═O β-lactum); 1720 cm⁻¹ C═O ester).

What is claimed is:

1. A process for preparing an azetidinone-thiazolidine derivative of the structure:

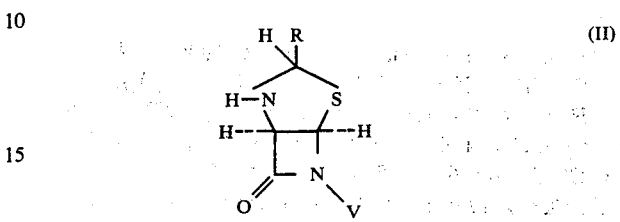

where R is a phenoxymethyl group and V is the residue:

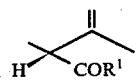

where R¹ is an alkoxy group having from 1 to 4 carbon atoms, wherein a compound of the structure:

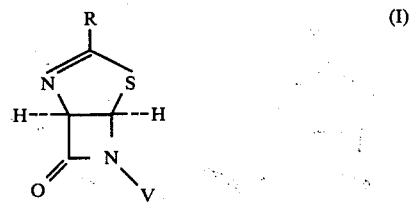

where R and V have the meanings given heretofore,
dissolved in a suitable solvent such as dioxane, tetrahydrofuran, methanol or ethanol, alone or in admixture is treated at a temperature of about 0° C with a solution of preferably anhydrous hydrochloric acid in a lower aliphatic alcohol and with a slight excess of sodium cyanoborohydride, keeping the reaction mass under stirring for 20–30 minutes, and after the excess of reagent is eliminated by adding a dilute acid, isolating and purifying a compound of the formula (II) thus formed.

2. A process as defined in claim 1, wherein R¹ is methoxy.

* * * * *